(12) United States Patent
Norton (10) Patent No.: US 12,076,228 B2
(45) Date of Patent: Sep. 3, 2024

(54) DEVICES AND METHODS FOR FIXATION AGAINST TISSUE

(71) Applicant: Biomet Manufacturing, LLC, Warsaw, IN (US)

(72) Inventor: Daniel R. Norton, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 308 days.

(21) Appl. No.: 17/490,931

(22) Filed: Sep. 30, 2021

(65) Prior Publication Data
US 2022/0104935 A1  Apr. 7, 2022

Related U.S. Application Data

(60) Provisional application No. 63/087,551, filed on Oct. 5, 2020.

(51) Int. Cl.
*A61F 2/08* (2006.01)

(52) U.S. Cl.
CPC ..... *A61F 2/0811* (2013.01); *A61F 2002/0817* (2013.01); *A61F 2002/0852* (2013.01); *A61F 2002/0882* (2013.01)

(58) Field of Classification Search
CPC ............ A61F 2/0811; A61F 2002/0817; A61F 2002/0852; A61F 2002/0882; A61F 2/0805; A61F 2002/0847
See application file for complete search history.

(56) References Cited

U.S. PATENT DOCUMENTS

| 5,300,077 | A | 4/1994 | Howell | |
|---|---|---|---|---|
| 5,570,706 | A | 11/1996 | Howell | |
| 6,254,604 | B1 | 7/2001 | Howell | |
| 6,440,134 | B1 * | 8/2002 | Zaccherotti | A61F 2/0811 606/232 |
| 6,514,274 | B1 | 2/2003 | Boucher et al. | |
| 7,500,983 | B1 * | 3/2009 | Kaiser | A61B 17/0401 606/232 |
| 7,601,165 | B2 | 10/2009 | Stone | |
| 9,186,241 | B2 * | 11/2015 | Walker | A61B 17/0401 |
| 9,216,078 | B2 * | 12/2015 | Conner | A61B 17/0401 |
| 10,085,740 | B1 * | 10/2018 | Anderson | A61B 17/0401 |
| 2012/0065731 | A1 * | 3/2012 | Justin | A61F 2/0811 623/13.14 |

* cited by examiner

*Primary Examiner* — Jerrah Edwards
*Assistant Examiner* — Kia Xiong White
(74) *Attorney, Agent, or Firm* — SCHWEGMAN LUNDBERG & WOESSNER, P.A.

(57) ABSTRACT

A device configured for use during a surgical procedure. The device can optionally include any one or combination of a first foot and a spine. The first foot can form at least a first edge at a first longitudinal end of the device. The first foot can be configured to seat the device on a tissue of a patient. The spine can be connected to the first foot and can have a longitudinal length extending from first foot toward a second longitudinal end of the device. The spine can include an eyelet adjacent to but offset from the first foot.

11 Claims, 10 Drawing Sheets

FIG. 6 ded on Oct. 5,
DEVICES AND METHODS FOR FIXATION AGAINST TISSUE

CLAIM OF PRIORITY

This application claims the benefit of U.S. Provisional Patent Application Ser. No. 63/087,551, filed on Oct. 5, 2020, the benefit of priority of which is claimed hereby, and which is incorporated by reference herein in its entirety.

TECHNICAL FIELD

The present application pertains generally, but not by way of limitation, to devices and methods used during a surgical procedure to repair or reconstruct a torn or otherwise damaged ligament or joint. More specifically, but not by way of limitation, the present application relates to devices for the fixation of suture or a graft.

BACKGROUND

The anterior cruciate ligament (ACL) is a three-dimensional structure with broad attachments and a continuum of fibers. These fibers are of different lengths, have different attachment sites, and are under different tensions. The ACL is a ligament frequently injured by patients such as during participation in sports activities. Such injuries cause instability in the knee joint which, when left untreated, may lead to degenerative arthritis. Because of this condition, ACL reconstruction may be required. Generally during ACL reconstruction, a substitute soft tissue ligament or graft is attached to the femur and/or tibia to facilitate regrowth and permanent attachment. Attachment of the graft can be via a tunnel through the femur and/or tibia. The substitute graft can include one or more graft bundles or strands that are tensioned prior to the femoral and/or tibial fixation.

Although many current substitutes for cruciate ligaments may not duplicate the complex orientation and operation of normal ACLs, they can operate to mimic the normal ACL operation effectively when they are placed properly. Various challenges are associated with orienting, affixing and otherwise properly placing the graft to mimic the normal ACL operation effectively while minimizing patient pain and discomfort. For example, abrasive wear of the graft should be avoided, and additionally, preserving a maximum amount of natural bone of the knee joint is desirable. It is another goal of ACL replacement procedures to create a tibial tunnel placement that may allow the implanted ACL to interact more normally with the posterior cruciate ligament (PCL).

Techniques have also been developed to repair the ligaments of shoulder and other ligaments.

Overview

The present application focuses on examples of fixation devices, also termed "buttons", "fixation buttons" or "suspensory fixation buttons" herein, these devices are designed to affix a suture and/or a graft to tissue including bone. As used herein the term "bone" can include any suitable bone of the human anatomy such a femur, tibia or humerus. In some examples, the disclosed devices can be used for reconstruction procedures such as those for the ACL or rotator cuff. However, other procedures and surgeries such as those with suture fixation to bone or tissue could be aided by the present devices disclosed herein. Thus, although the present application is described in reference to an ACL and a rotator cuff reconstruction, other applications for the devices disclosed herein are contemplated. For example, the devices discussed herein can be used in a repair of the acromioclavicular joint (AC) of the shoulder.

Examples of ACL repair surgery and instrumentation are described in U.S. Pat. No. 5,300,077 to Howell, U.S. Pat. No. 5,570,706 to Howell, U.S. Pat. No. 6,254,604 to Howell, U.S. Pat. No. 7,601,165 to Stone and U.S. Pat. No. 9,216,078 to Conner et al., which are each hereby incorporated by reference herein in their entirety. Examples of rotator cuff repair surgery are described in U.S. Pat. No. 6,514,274 to Boucher, which is incorporated by reference in its entirety.

The present inventor has recognized, among other things, that a problem to be solved can include a risk of inadvertently capturing, pulling or otherwise irritating tissue with fixation buttons in common use at present. For example, during ACL reconstruction, current fixation buttons are pulled through a bone tunnel in the femur and then are flipped 90 degrees to fixate on the lateral cortex of the femur. However, with the design of these buttons there is a risk that the button can be inadvertently pulled partially or fully through soft tissue (iliotibial (IT) band, etc.) that is beyond the lateral cortex of the femur. This can result in improper seating of the button and/or damage to the tissue that becomes trapped between the button and the lateral cortex.

The present subject matter can help provide a solution to this problem, such as by providing fixation buttons that are shaped to reduce the risk of passage into or through the soft tissue. Thus, a leading edge of the button can be offset from a suture that is used to shuttle the button through the bone tunnel. Additionally, the leading edge can be wider than a guidewire that creates the incision through soft tissues. The button can also be constructed such that the suture runs through an eyelet in a thin spine, minimizing the tendency for the suture to expand the puncture in the soft tissue. Furthermore, the geometry of the button results in the button more consistently rotating to a deployed position against the lateral cortex when contacted against soft tissue instead of passing into or through the puncture in the soft tissue.

The present inventor has further recognized, among other things, that another problem to be solved can include many current buttons utilize a fixed loop connection or several loop connection with an implant such as a bone plug or graft. These types of connections can be complex for a surgeon to manage. Thus, significant practice and skill can be important to manage them. For example, the surgeon may drill through a bone plug, pass suture through the plug to create the fixed loop and pass the button through the fixed loop to create a "luggage tag" type connection with the graft. This technique is complicated and relies on the surgeon's ability to manage suture and complete the assembly process in vivo.

Thus, the present inventor proposes a simpler way for the surgeon to start with an open loop (also termed an adjustable loop herein), pass suture through the bone plug, and then close the loop without the use of a secondary fixed loop or complicated suture management.

This overview is intended to provide an overview of subject matter of the present patent application. It is not intended to provide an exclusive or exhaustive explanation of the invention. The detailed description is included to provide further information about the present patent application.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present teachings provide various buttons and other components for fixation to tissue. The button can be used herein with other instruments known in the art for ACL or other ligament repair, joint repair or the like. Various button configurations according to the present disclosure are illustrated in FIGS. 1-5 and discussed in further detail below.

Figure 1:
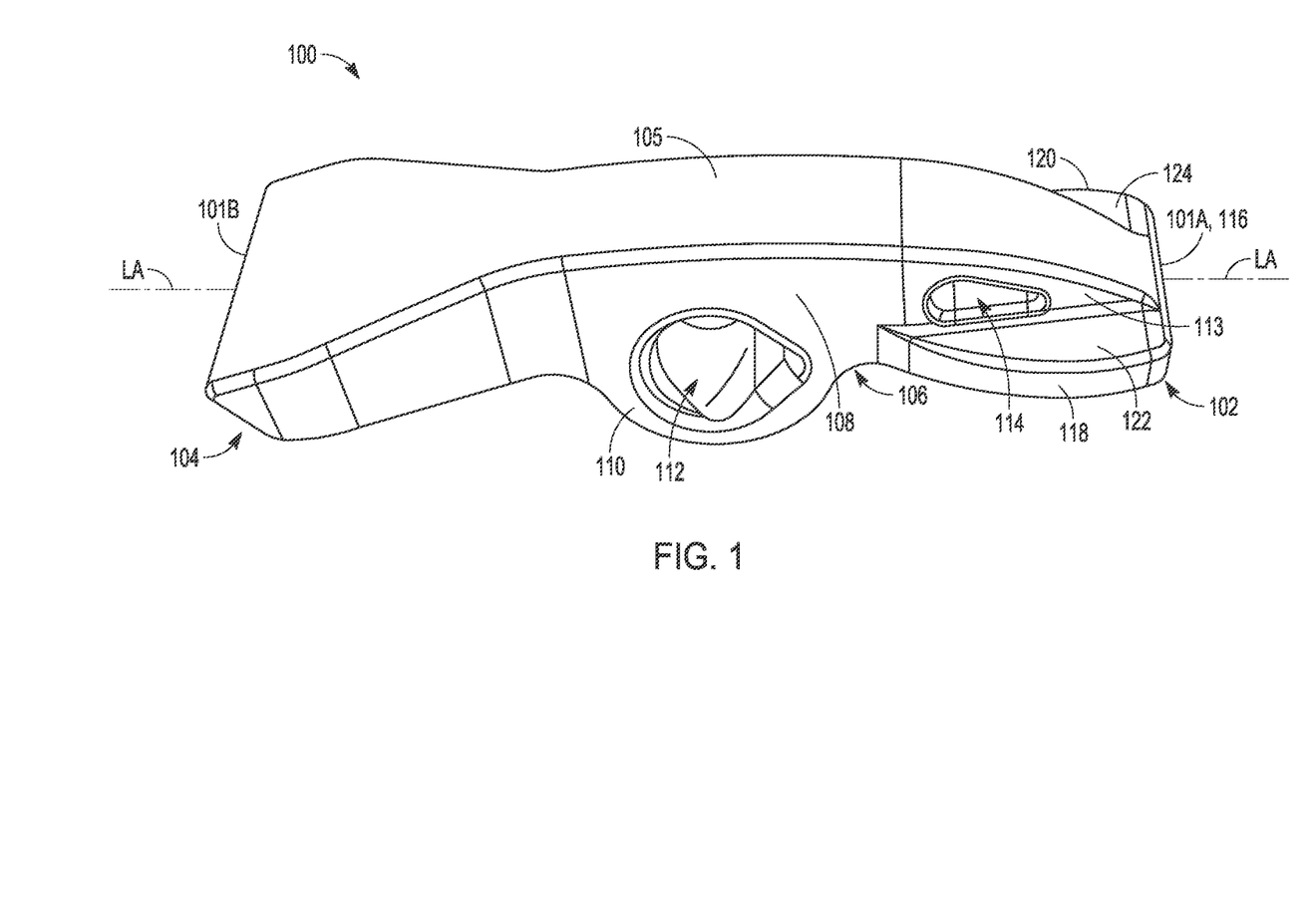
FIG. 1 is a perspective view of a button according to an example of the present application.
Figure 1A:
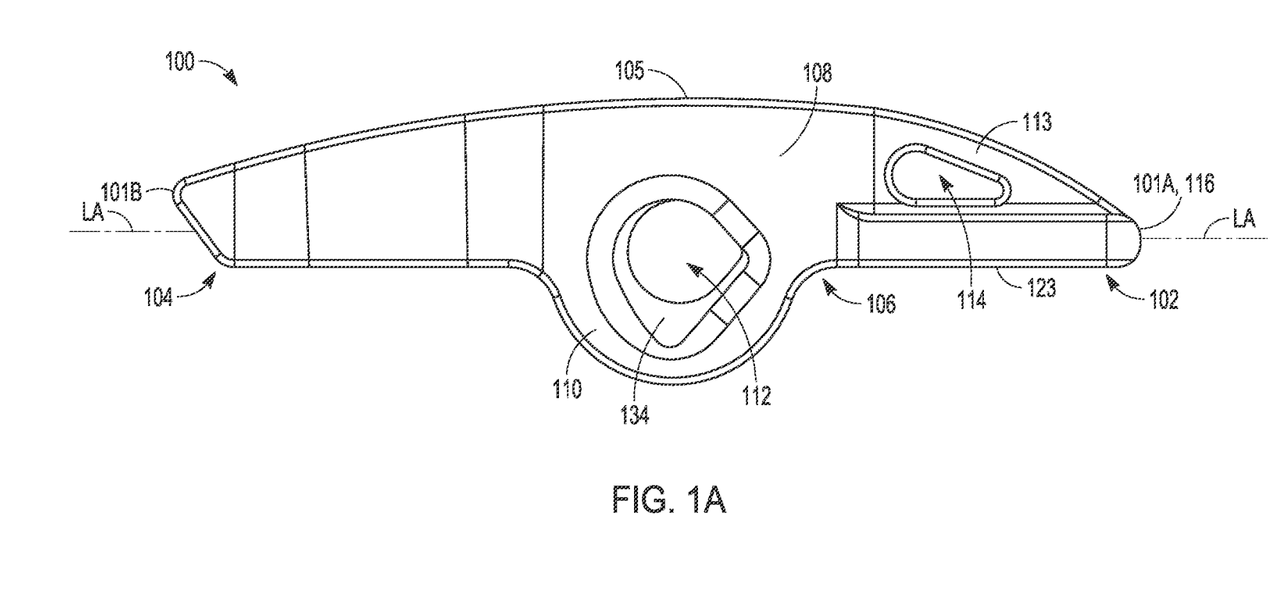
FIG. 1A is a planar side view of the button of FIG. 1.
Figure 1B:
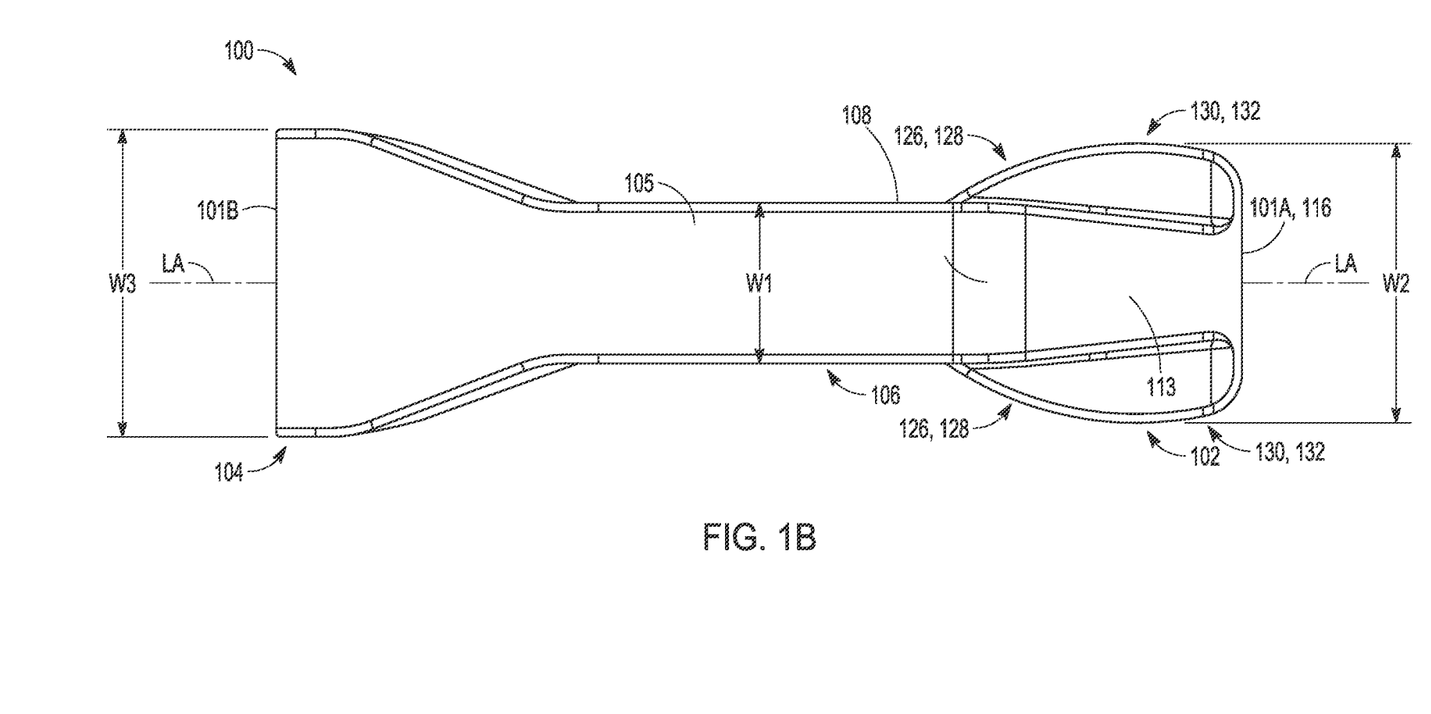
FIG. 1B is a planar top view of the button of FIG. 1.

FIG. 1 shows a perspective view of an example button 100. FIGS. 1A and 1B show planar views of different sides of the button 100. The button 100 can include a first foot 102, a second foot 104 and a spine 106. The spine 106 can include a central portion 108, a projection 110, a first eyelet 112 and a second eyelet 114. The first foot 102 can include a first edge 116, a second edge 118, a third edge 120 and surfaces 122 and 124.

The button 100 can include longitudinal length and can extend along a longitudinal axis LA in a symmetrical configuration from a first longitudinal end 101A to a second longitudinal end 101B. More particularly, the first foot 102, the spine 106 and the second foot 104 can be arranged to extend along the longitudinal axis LA. The spine 106 can be arranged between the first foot 102 and the second foot 104 such that the first foot 102 can form the first longitudinal end 101A of the button 100 and the second foot 104 can form the second longitudinal end 101B of the button 100.

The spine 106 can be connected to the first foot 102 and can have a longitudinal length extending from the first foot 102 toward the second longitudinal end of the button 100. As shown in FIGS. 1 and 1A, the spine 106 can have a proximal surface 105 with an arcuate curvature along substantially an entirety of the longitudinal length from the first foot 102 to the second longitudinal end 101B. The spine 106 can be connected to the first foot 102 and the second foot 104. Such connection can be integral, for example. Although illustrated as having the second foot 104 in the example of FIGS. 1-1B, the button 100 may not have a second foot according to some examples.

As shown in FIG. 1B, the central portion 108 of the spine 106 can comprise a region of reduced width W1 as measured in a direction transverse to the longitudinal axis LA as measured relative to a width W2 of the first foot 102 and a width W3 of the second foot 104. Put another way, the first foot 102 can have the width W2 in a direction transverse to the longitudinal length that exceeds the width W1 of the spine 106 in the direction transverse to the longitudinal length.

As shown in FIG. 1A, the central portion 108 can include the projection 110. As a result of the projection 110 and the arcuate curvature of the proximal surface 105 opposing the projection 110, the spine 106 can have an increased thickness relative to thicknesses of the first foot 102 and the second foot 104. The thicknesses including can be measured in a direction transverse to the longitudinal axis LA and transverse to the widths W1, W2 and W3 (shown in FIG. 1B). As a result of the arcuate curvature of the proximal surface 105 and the projection 110, the thickness of the spine 106 at the central region 108 can exceed a thickness of the spine adjacent the first edge 116 and at the second longitudinal end 101B.

The spine 106 can be configured to form the first eyelet 112 in the central portion 108. The projection 110 can form at least a portion of the first eyelet 112 according to the example of FIG. 1A. The central portion 108 can be partially formed by the projection 110. The projection 110 can form a part of a distal surface of the spine 106. The spine 106 can extend forward from the central portion 108 and can be located above and connected to the first foot 102. This forward portion 113 of the spine 106 can connect with the first foot 102 and can form the second eyelet 114 above and adjacent to the first foot 102. The second eyelet 114 can be offset from the edge 116 and the first eyelet 112 in the thickness direction (the direction transverse to the longitudinal axis LA).

The first foot 102 can form the first edge 116 at a first longitudinal end of the button 100. As shown in FIG. 1B, the first edge 116 of the first foot 102 can comprise a leading edge of the button 100 as further discussed herein. The first edge 116 can be located at a longitudinal end of the button 100. The first edge 116 can be filleted, chamfered or otherwise configured as desired according to some examples. As shown in FIG. 1B, the forward portion 113 of the spine 106 can extend to form a portion of the first edge 116 with the first foot 102. Thus, the first foot 102 and the spine 106 can have the fillet (or another feature) along the first edge 116 as shown in FIG. 1B. The forward portion 113 of the spine 106 can have a progressively decreasing thickness moving longitudinally from the central portion 108 toward the first edge 116 as shown in FIG. 1A.

The first foot 102 can be configured to seat the button 100 on a tissue of the joint of the patient as further discussed and illustrated herein. The second edge 118 can connect with the first edge 116 and can extend rearward thereof along the longitudinal length. The third edge 120 can oppose the second edge 118 across the longitudinal axis LA in the width dimension. The third edge 120 can connect with the first edge 116 and can extend rearward thereof along the longitudinal length. The second edge 118 and/or the third edge 120 can have a fillet or other feature as desired. The surface 122 can be located between the spine 106 and the second edge 118. The surface 124 can oppose the surface 122 across the longitudinal axis LA. Thus, the surface 124 can be located between the spine 106 and the third edge 120. The surfaces 122 and 124 can be substantially flat, chamfered, curved, etc. as desired. The surfaces 122 and 124 can comprise proximal surfaces for the button 100 and can be generally opposed by one or more bone or tissue facing surfaces 123 of the first foot 102 as shown in FIG. 1A.

As shown in FIG. 1B, the first foot 102 can have a spade or truncated spade shape. In particular, the first foot 102 (and, in particular, the second edge 118 and the third edge 120) can have a first taper 126 along a first portion 128 of the longitudinal length such that the width of the first foot increases along the first portion 128 of the longitudinal length. The first foot 102 (and, in particular, the second edge 118 and the third edge 120) can have a second taper 130 along a second portion 132 of the longitudinal length such that the width of the first foot 102 decreases along the second portion 132 of the longitudinal length to the first edge 116. The first taper 126 can connect to the second taper 130. The shape of the first foot 102 with the edges 116, 118, 120, tapers 126, 128 can provide the button 100 with a blunt edge configuration and a region of increased width (relative to the central portion 108) at a longitudinal end portion of the button 100.

As shown in the example of FIGS. 1-1B, the second foot 104 can form the second opposing longitudinal edge 101B at the second longitudinal end that opposes the first edge 116. The second foot 104 can have a configuration similar to that of the first foot 102. Thus, the second foot 104 can have a width in a direction transverse to the longitudinal length of the button 100 that exceeds the width of the spine 106. The second foot 104 additionally can have tapering similar to that as described with regard to the first foot 102.

The second eyelet 114 can be tear dropped shaped with a narrower region facing the first longitudinal end 101A. The first eyelet 112 can have a tear drop shape having a narrower region facing and closer to the first foot 102. The central portion 108 of the spine 106 that forms the first eyelet 112 can have a fillet, chamfer or other features as desired along desired edges thereof. For example, a fillet 134 (FIG. 1A) can be along at least a portion of the first eyelet 112. This portion can be an edge facing the first longitudinal end 101A (including the first foot 102) and/or along an edge facing the projection 110.

Figure 2A:
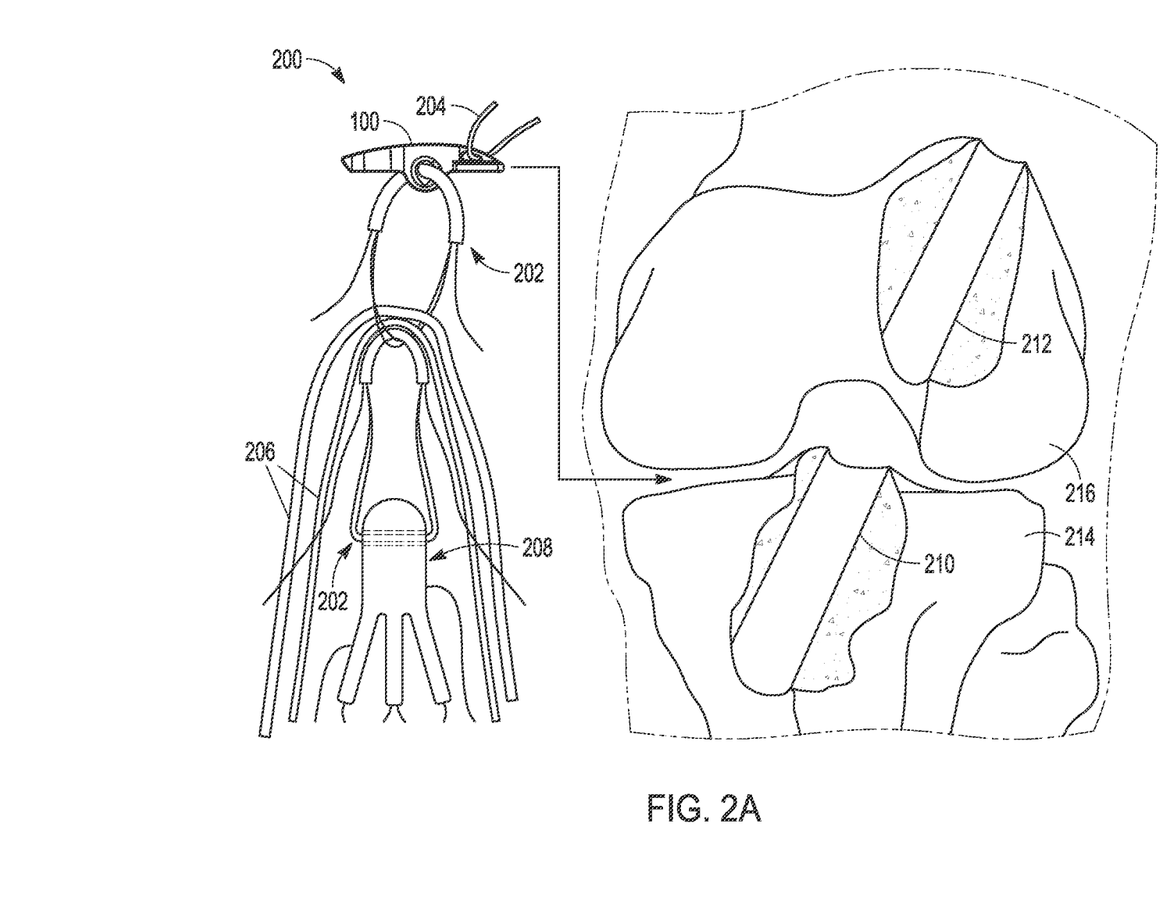
FIGS. 2A and 2B are views depicting an exemplary ACL reconstruction procedure using the button of FIGS. 1-1B and other devices according to an example of the present application.
Figure 2B:
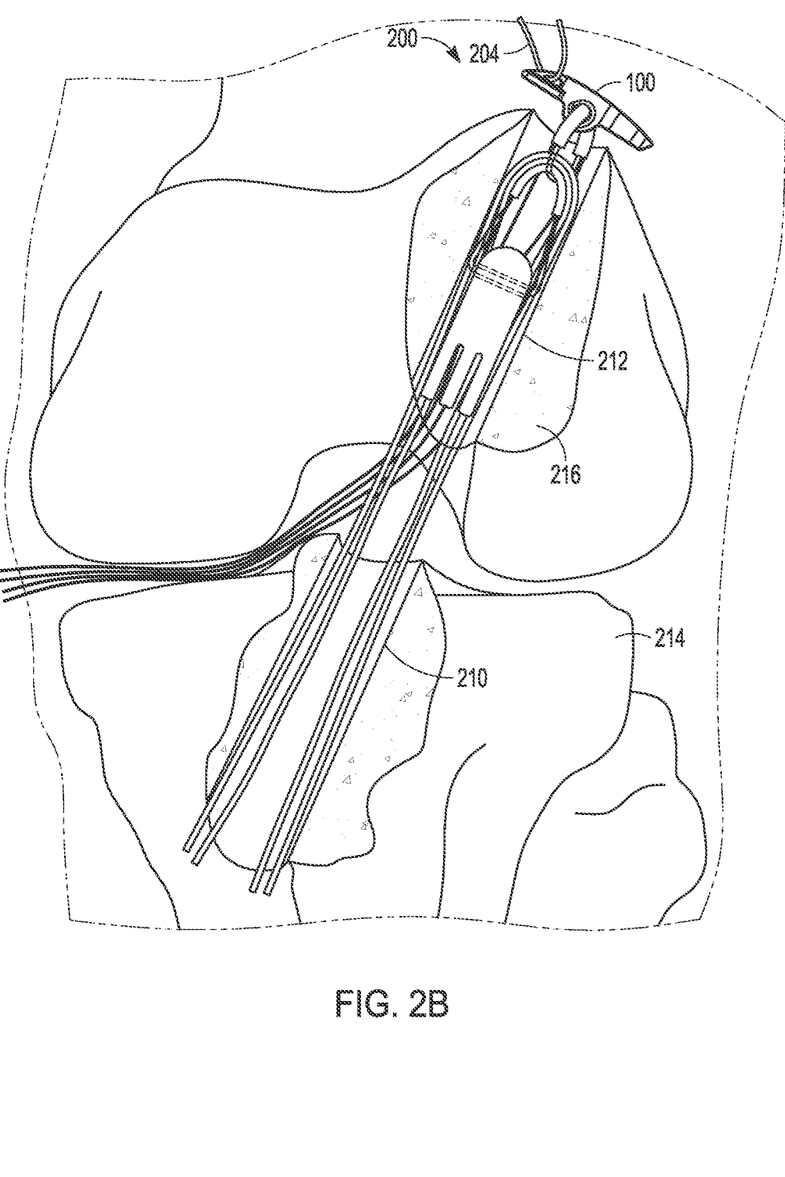

FIGS. 2A and 2B show an application of the button 100 as part of a system 200 for ACL joint reconstruction. As shown in FIG. 2A, in addition to the button 100, the system 200 can include one or more suture constructs 202 (also referred to a loops or loop herein), guide suture 204, one or more grafts 206 and a fixation member 208 such as a plug or anchor. FIG. 2B shows the system 200 deployed within a tibial tunnel 210 and a femoral tunnel 212.

In brief, the tibial and femoral tunnel 210 and 212 can be formed using known instrumentation such as those disclosed in the applications incorporated herein by reference. The tibial tunnel 210 can be formed or drilled into a tibia 214 and the femoral tunnel 212 can be formed or drilled into a femur 216, as shown for example in FIGS. 2A and 2B.

The tibial tunnel 210 can include a first end or entrance and a second end or exit opposite of a joint space between the femoral and tibial tunnels. Similarly, femoral tunnel 212 can include a first end or entrance adjacent joint space and can include a second end or exit, or can be formed as a blind tunnel. In one exemplary configuration, the tibial tunnel 210 can be formed at about a 45 degree angle to a longitudinal axis of the tibia, as is also known in the art. The tunnels 210 and 212 can be formed in any appropriate manner, such as those generally known in the art, and will not be described in further detail herein.

One or more components of the system 200 can be passed through the tunnels 210 and 212 as illustrated in FIG. 2B. The system 200 comprises a bundle that can include the one or more grafts 206 looped around an adjustable self-locking flexible member or the one or more suture constructs 202.

The one or more grafts 206 can thus include, two graft strands, three graft strands, four graft strands, etc. extending from the one or more suture constructs 202. It should be appreciated that various other graft configurations can be used, including more or less graft loops and/or individual graft strands secured together at one end. In one exemplary aspect, one or more grafts 206 can include a synthetic or natural graft, such as an autograft or an allograft.

The one or more suture constructs 202 can have a hollow flexible outer member with a tunnel or passage therethrough allowing parts of the suture to pass therethrough. Ends of the suture can be pulled or tensioned as desired to adjust the one or more suture constructs 202 as desired. This allows for adjustment of the loops formed by the one or more suture constructs 202 and also adjusts the one or more grafts 206 that are looped thereto. The one or more suture constructs 202 can be configured to cause the suture(s) passing through the tunnel or passage to "automatically" lock in a reduced size or smaller diameter configuration without the use of a knot. A further discussion of the one or more suture constructs 202 is provided in U.S. patent Ser. No. 11/541,506 filed on Sep. 29, 2006 entitled "Method and Apparatus for Forming a Self-Locking Adjustable Suture Loop" assigned to Biomet Sports Medicine, LLC, now U.S. Pat. No. 7,601,165, and the disclosure of which is incorporated by reference herein.

During the procedure, one or more suture constructs 202 can be connected to the button 100 such as via the first eyelet 112. The one or more grafts 206 can be looped around the one or more suture constructs 202. The guide suture 204 can be passed through the femoral tunnel 212 and then through the tibial tunnel 210. The guide suture 204 can then be connected to the button 100 such as through the second eyelet 114. The guide suture 204 can then be pulled back through one or more of the tibial tunnel 210 and the femoral tunnel 212. This results in the configuration shown in FIG. 2B.

The button 100 can be constructed to facilitate femoral fixation or retention of the system 200 including the one or more grafts 206 relative to the femoral tunnel 212. The fixation member 208 can be deployed into the femoral tunnel 212, the tibial tunnel 210 and/or against the tibia to facilitate fixation and tensioning of the one or more grafts 206 against the bone. The one or more grafts 206 can be passed through the loops of the one or more suture constructs. Tensioning of the ends of the one or more suture constructs 202 applies tension to the loops, thus pulling the one or more grafts 206 into the tibial and femoral tunnels 210, 212, as shown in FIG. 2B.

The fixation member 208 can include further anchors or plugs not specifically shown. These fixation members can be configured to facilitate tensioning or other procedural aspects as known in the art. Thus, the construction of the fixation member 208 and its location within the femoral tunnel 212 in FIG. 2B is purely exemplary. Other constructions and locations (and indeed further fixation members) are contemplated by the present application.

Figure 3A:
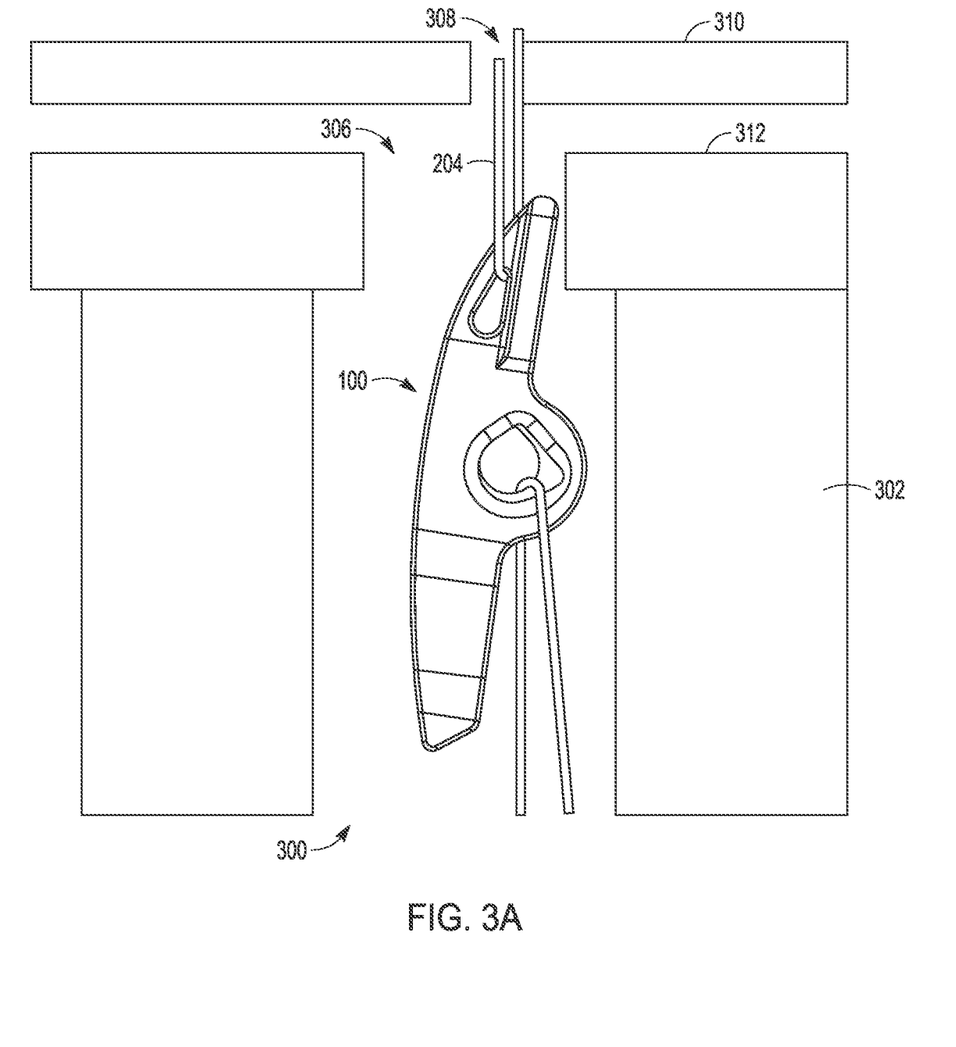
FIGS. 3A-3C are views of the button of FIGS. 1-1B being deployed through a bone tunnel and positioned as desired adjacent soft tissue according to an example of the present application.
Figure 3B:
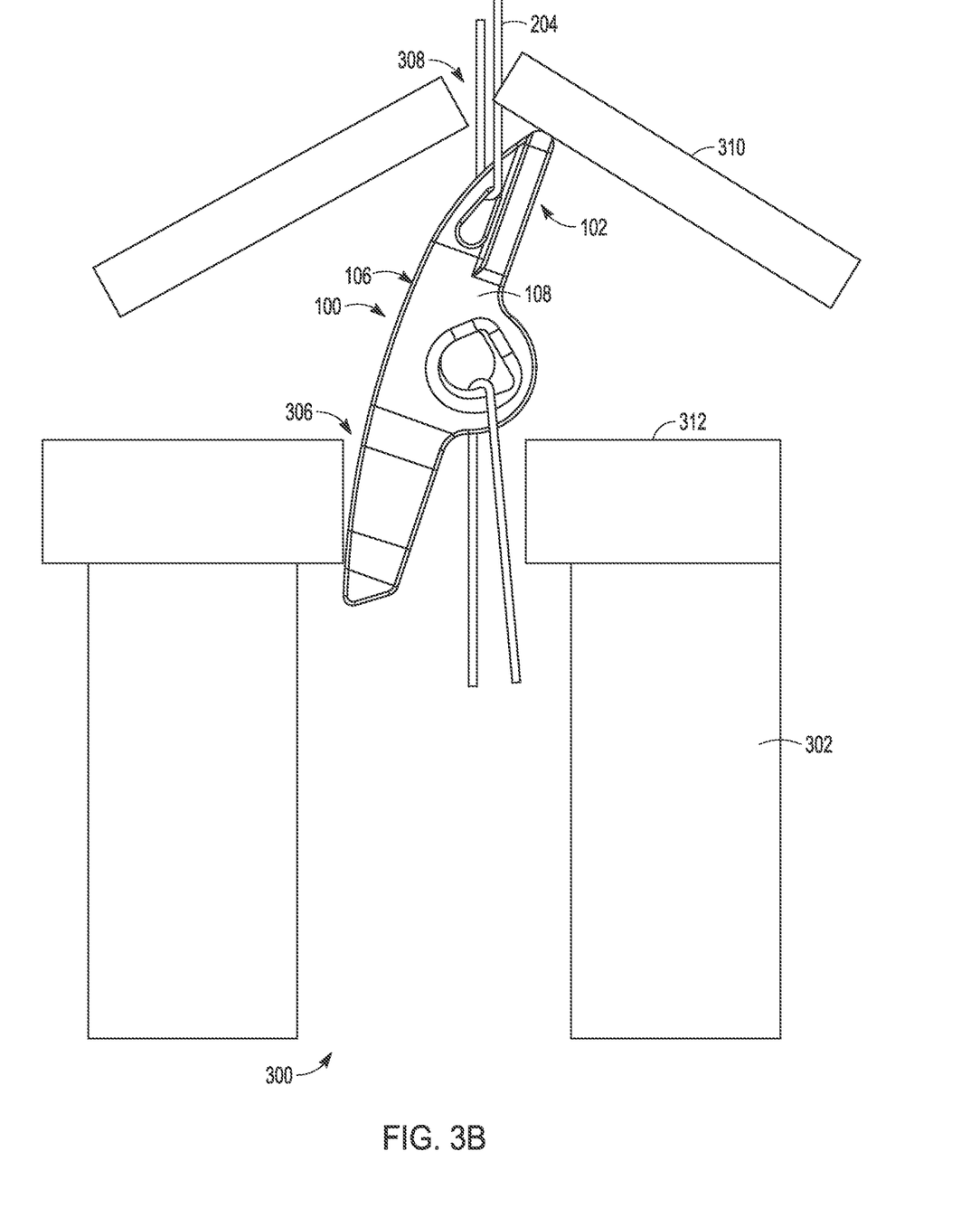
Figure 3C:
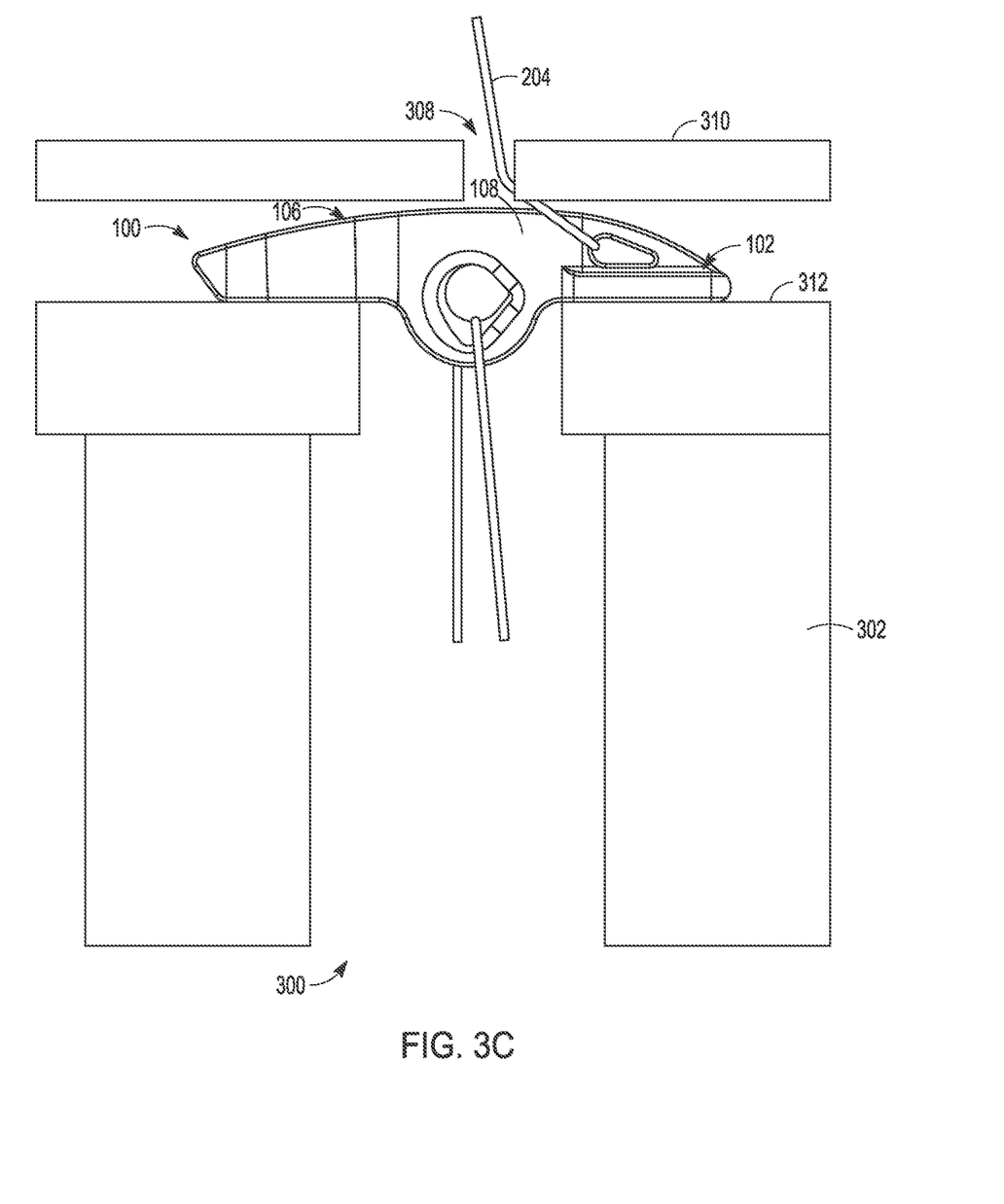

FIGS. 3A-3C show deployment of the button 100 through a bone tunnel 300 such as the femoral tunnel 212 of FIGS. 2A and 2B. As shown in FIG. 3A-3C, the guide suture 204 can be utilized to pass the button 100 through the bone tunnel 300. The button 100 can be connected to the sutures, and hence the grafts as previously described and illustrated. As guided by the guide suture 204, the button 100 can have a first configuration that can allow the button 100 to be passed through tunnel 300 in the bone 302 as shown in FIG. 3A.

As shown in FIGS. 3A-3C, the guide suture 204 can pass through an opening 306 (exit) to the bone tunnel 300 and can pass through a second opening 308 in a soft tissue 310. This soft tissue 310 can be external to an lateral cortex of the bone 302 and can comprise, for example, an iliotibial band (IT) or other soft tissue.

As shown in FIGS. 3B and 3C, the configuration of the button 100, with e.g., the blunt edge configuration and the region of increased width (relative to the central portion 108) at the longitudinal end portion (the first foot 102) of the button 100 can result in the button 100 being discouraged from being drawn into the second opening 308 or into the soft tissue 310. Furthermore, the shape of the first foot 102 and the spine 106 (including the filleted leading edge, the offset eyelet from the leading edge, the curved proximal surface, etc.) can facilitate rotation and seating of the button 100 against an outer surface 312 of the bone 302 as shown in FIGS. 3B and 3C.

Thus, the button 100 can be sized and shaped to include a first profile that allows insertion through the bone tunnel as shown in FIG. 3A, and a second profile that allows engagement with a positive locking surface upon rotation outside of the tunnel as shown in FIGS. 3B and 3C.

As discussed previously, prior buttons had a risk of inadvertently capturing, pulling or otherwise irritating tissue 310. For example, these buttons had a risk that the button could be inadvertently pulled partially or fully through soft tissue 310. This could result in improper seating of the button and/or damage to the tissue that becomes trapped between the button and the lateral cortex.

The present button 100 can be shaped to reduce the risk of passage into or through the soft tissue 310. Thus, the first edge 116 of the button can be offset from the suture 204 that is used to shuttle the button 100 through the bone tunnel 300. Additionally, the first edge 116 (comprising the leading edge during deployment as illustrated in FIGS. 2A-3C) can be wider than a guidewire that creates the incision (opening 308) through soft tissues. The button 100 can also be constructed such that the suture runs through the second eyelet 114 in the relatively less wide spine 106. These arrangements and configurations can minimize the tendency for the suture 204 to expand the puncture in the soft tissue 310. Furthermore, the geometry of the button 100 results in the button 100 more consistently rotating to the deployed position of FIG. 3C against the bone 302 of the lateral cortex when contacted against soft tissue 310 as illustrated in FIG. 3B instead of passing into or through the second opening 308 in the soft tissue 310.

Figure 4:
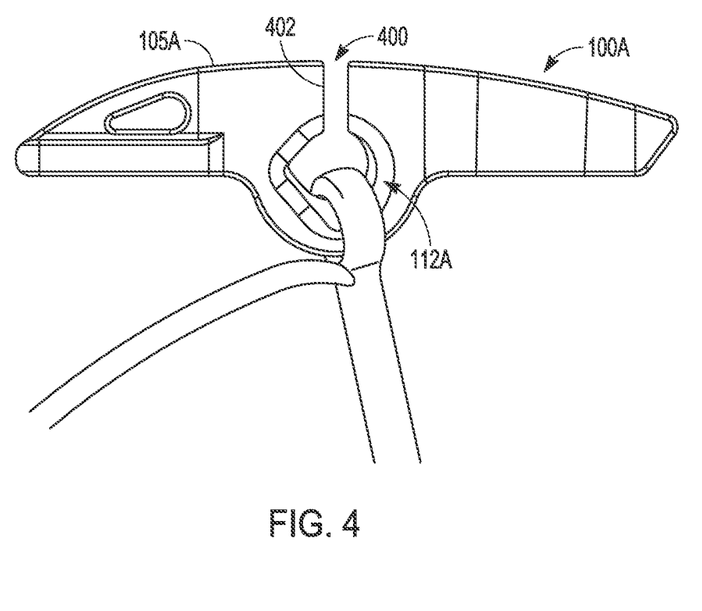
FIG. 4 is a perspective view of another example of a button having an eyelet with an opening or slit along a top side thereof.
Figure 5:
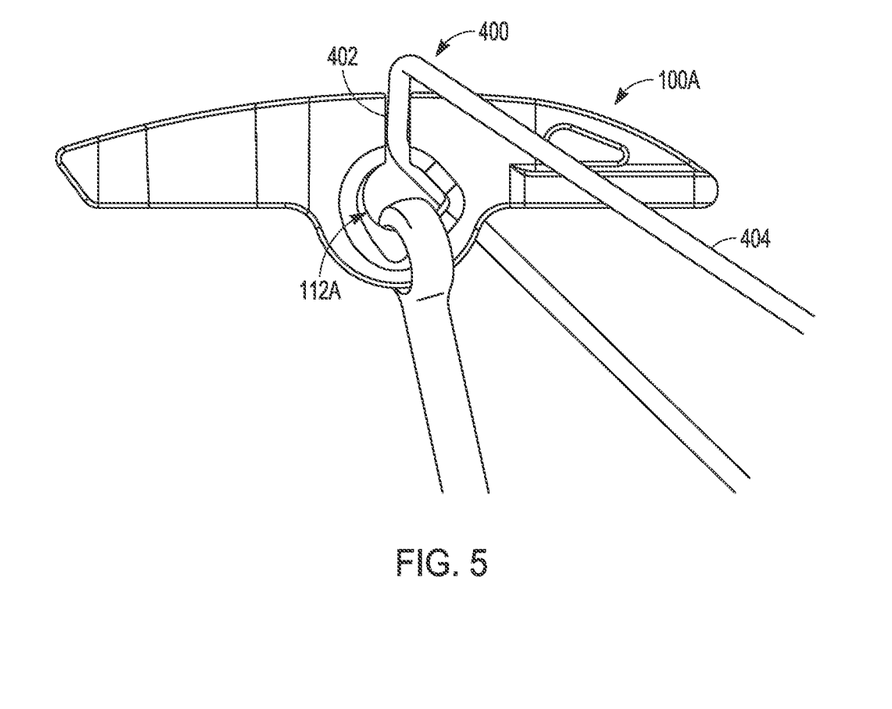
FIG. 5 shows the button of FIG. 4 receiving suture via the opening or slit to form an adjustable loop according to an example of the present application.

FIGS. 4 and 5 show a button 100A according to another example. The button 100A can be configured in a manner identical to that of the button 100 of FIGS. 1-3C with the exception that the first eyelet 112A has an opening 400 formed by a slit 402 that communicates with the first eyelet 112A from a proximal surface 105A of the button 100A. Thus, spine 106A of the button 100A forms the opening 400 and the slit 402 that communicate with the first eyelet 112A. Thus, the button 100A includes an additional opening to the first eyelet 112A as compared with the button 100 with the first eyelet 112.

FIG. 5 illustrates that the slit 402 and the opening 400 allow a suture 404 such as a loop of the same suture structure or another suture, a graft, or another component to be selectively connected to the button 100A. This connection of the suture 404 can occur with relative ease as compared with the prior art and can occur in vivo or prior to deployment of the button 100A into patient, for example.

Allowing for connection of the suture 404 provides a simpler way for the surgeon to start with an open loop (also termed an adjustable loop herein), pass a portion of the suture through the bone plug, and then pass other portions of the suture around or through desired anatomy, and then close the loop with the other portion of the suture by simply snapping it through the slit 402 without the use of a secondary fixed loop or complicated suture management.

This process should be contrasted with current techniques (even those described and illustrated in FIGS. 2A and 2B herein), which can be complex for a surgeon to manage and include the use of multiple interconnected loops of suture and graft.

Figure 6:
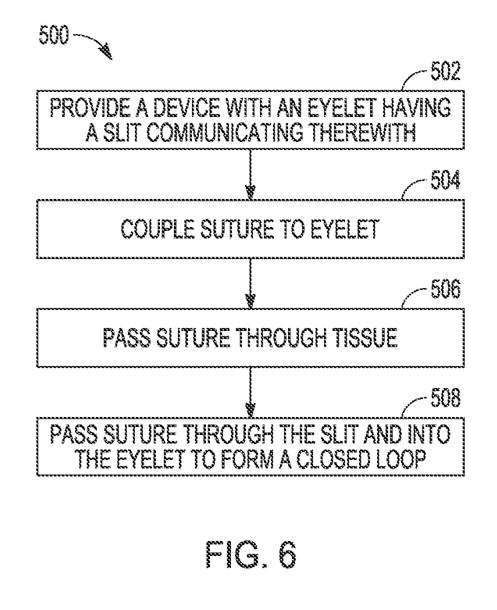
FIG. 6 is a flow chart of a method of utilizing a button such as that of FIGS. 4 and 5 according to an example of the present application.

FIG. 6 shows an exemplary method 500 of repair of a joint of a patient. The method can include the step 502 of providing a device having an eyelet with a slit forming an opening thereto. The device can be configured to be positioned within the joint on tissue of the patient. The method 500 can include the step 504 of coupling a suture to the eyelet and the step 506 of passing the suture through the tissue of the patient. The method 500 can include the step 508 of passing the suture through the slit that provides the opening and into the eyelet to form a closed loop with the tissue passed through the tissue.

According to further examples, the method 500 can include adjusting a size of the closed loop to draw the tissue together and toward the device. The device can include a spine and a first foot coupled to the spine and positioned at a first longitudinal end of the device. The spine can include a first eyelet configured to couple with the one or more sutures and a second eyelet configured to couple with the loop. The first foot can have a width of a larger dimension relative to a corresponding width of the spine as measured relative to a longitudinal axis of the device. The width of the first foot and the width of the spine can be measured in a direction transverse to a longitudinal axis of the device. The increased width of the first foot can be configured to deter a passage of the device through a tunnel in soft tissue used for passage of the suture to the joint of the patient.

According to one example, the method 500 can be applied to AC joint reconstruction. The following steps can be performed. Drill a hole through the clavicle to create the bone tunnel. Pass the loop through the clavicle. Pass the loop around a coracoid. Pass the loop back through the clavicle via the bone tunnel. Pass the loop into the eyelet of the device via the slit that creates the opening thereto.

VARIOUS NOTES & EXAMPLES

Example 1 can include a device configured for use during a surgical procedure. The device can optionally include any one or combination of a first foot and a spine. The first foot can form at least a first edge at a first longitudinal end of the device. The first foot can be configured to seat the device on a tissue of a patient. The spine can be connected to the first foot and can have a longitudinal length extending from first foot toward a second longitudinal end of the device. The spine can include an eyelet adjacent to but offset from the first foot.

Example 2 is the device of Example 1, optionally the first foot can have a width in a direction transverse to the longitudinal length that exceeds a width of the spine in the direction transverse to the longitudinal length.

Example 3 is the device of Example 2, optionally the first foot can have a first taper along a first portion of the longitudinal length such that the width of the first foot increases along the first portion of the longitudinal length.

The first foot can have a second taper along a second portion of the longitudinal length such that the width of the first foot decreases along a second portion of the longitudinal length to the first edge.

Example 4 is the device of any one or combination of Examples 1-3, optionally the first foot and the spine together can form the first edge, and the first foot and spine can have a fillet along the first edge.

Example 5 is the device of any one or combination of Examples 1-4, optionally a portion of the spine that connects with the first foot can have a decreasing thickness moving longitudinally toward the first edge as measured in a direction transverse to the longitudinal length.

Example 6 is the device of any one or combination of Examples 1-5, optionally further comprising a second foot connected to the spine and forming the second longitudinal end of the device. The second foot can form a second edge at the second longitudinal end that opposes the first edge.

Example 7 is the device of Example 6, optionally the second foot can have a width in a direction transverse to the longitudinal length that exceeds the width of the spine in the direction transverse to the longitudinal length, the second foot can have a first taper along a first portion of the longitudinal length such that the width of the second foot increases along the first portion of the longitudinal length, and the second foot can have a second taper along a second portion of the longitudinal length such that the width of the second foot decreases along a second portion of the longitudinal length to the second edge.

Example 8 is the device of any one or combination of Examples 1-7, optionally the spine can have a proximal surface with an arcuate curvature along substantially an entirety of the longitudinal length from the first foot to the second longitudinal end.

Example 9 is the device of any one or combination of Examples 1-8, optionally a central portion of the spine has a thickness that exceeds a thickness of the spine adjacent the first edge and at the second longitudinal end, and the central portion can be configured to form a second eyelet.

Example 10 is the device of Example 9, optionally the central portion can be partially formed by a projection that forms a part of a distal surface of the spine, the projection can be configured to seat the device in a tunnel through the tissue of the patient.

Example 11 is the device of any one or combination of Examples 9-10, optionally the central portion that forms the second eyelet can have a fillet along at least a portion of the second eyelet facing the first foot of the device and along a portion facing the projection.

Example 12 is the device of any one or combination of Examples 9-11, optionally at least one of the first eyelet and the second eyelet can be tear-drop shaped.

Example 13 is the device of any one or combination of Examples 9-12, optionally the spine can be configured to form a second eyelet, and the spine can form a slit that forms an opening to communicate with the second eyelet.

Example 14 is a system for use during a surgical procedure. The system can optionally include any one or combination of a loop; one or more sutures; and a device. The device can be configured to be positioned within a patient. The device can optionally include a spine and a first foot coupled to the spine and positioned at a first longitudinal end of the device. The spine can optionally include a first eyelet configured to couple with the one or more sutures and a second eyelet configured to couple with the loop. The first foot can have a width of a larger dimension relative to a corresponding width of the spine along a longitudinal axis of the device. The width of the first foot and the width of the spine can be measured in a direction transverse to a longitudinal axis of the device. The increased width of the first foot can be configured to deter a passage of the device through a tunnel in soft tissue used for passage of the one or more sutures.

Example 15 is the system of Example 14, optionally the spine can have a slit that forms an opening that communicates with the second eyelet from a proximal surface of the device, and the loop can comprise an adjustable loop that can be passed through at least three openings of the second eyelet including the opening into the second eyelet.

Example 16 is the system of any one or combination of Examples 14-15, optionally further comprising a graft, wherein the graft is coupled to the device via the loop.

Example 17 is the system of any one or combination of Examples 15-16, wherein the proximal surface with an arcuate curvature along substantially an entirety of the longitudinal axis of the device.

Example 18 is a method of surgically repairing damage to a patient. The method can optionally include any one or combination of providing a device having an eyelet with an opening thereto formed by a slit that passes through a portion of the device to communicate with the eyelet, wherein the device is configured to be positioned on tissue of the patient; coupling a first part of a suture to the eyelet; passing a suture through the tissue of the patient; and passing a second part of the suture through the slit that provides the opening and back into the eyelet to form a closed loop for the suture.

Example 19 is the method of Example 18, optionally further comprising adjusting a size of the closed loop to draw the tissue together and toward the device.

Example 20 is the method of any one or combination of Examples 18-19, optionally the device includes a spine and a first foot coupled to the spine and positioned at a first longitudinal end of the device, the spine includes a first eyelet configured to couple with the one or more sutures and a second eyelet configured to couple with the loop, wherein first foot has a width of a larger dimension relative to a corresponding width of the spine along a longitudinal axis of the device, the width of the first foot and the width of the spine are measured in a direction transverse to a longitudinal axis of the device, and wherein the increased width of the first foot is configured to deter a passage of the device through a tunnel in soft tissue used for passage of the one or more sutures.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more," In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A device configured for use during a surgical procedure, the device comprising:
    a first foot forming at least a first edge at a first longitudinal end of the device, wherein the first foot is configured to seat the device on a tissue of a patient and has a first proximally facing surface and a second proximally facing surface;
    a spine connected to the first foot and having a longitudinal length extending from first foot toward a second longitudinal end of the device, wherein the spine includes a first eyelet adjacent the first foot and proximal of the first proximally facing surface and the second proximally facing surface, wherein the spine has a proximal surface with a convex arcuate curvature along substantially an entirety of the longitudinal length from the first longitudinal end to the second longitudinal end, wherein a central portion of the spine has a thickness that exceeds a thickness of the spine at the first longitudinal end and at the second longitudinal end, and wherein the central portion is partially formed by a projection that forms a part of a distal surface of the spine and the projection at least partially forms a second eyelet of the spine; and
    a second foot connected to the spine and forming the second longitudinal end of the device, wherein the second foot forms a second edge at the second longitudinal end that opposes the first edge, wherein the second foot and the first foot each have a width in a direction transverse to the longitudinal length that exceeds the width of the spine in the direction transverse to the longitudinal length, wherein the width of the second foot exceeds the width of the first foot.

2. The device of claim 1, wherein the first foot has a first taper along a first portion of the longitudinal length such that the width of the first foot increases along the first portion of the longitudinal length, and wherein the first foot has a second taper along a second portion of the longitudinal length such that the width of the first foot decreases along a second portion of the longitudinal length to the first edge.

3. The device of claim 1, wherein the first foot and the spine together form the first edge, and wherein the first foot and spine have a fillet along the first edge.

4. The device of claim 1, wherein the second foot has a first taper along a first portion of the longitudinal length such that the width of the second foot increases along the first portion of the longitudinal length, and wherein the second foot has a second taper along a second portion of the longitudinal length such that the width of the second foot decreases along a second portion of the longitudinal length to the second edge.

5. The device of claim 1, wherein the projection is configured to seat the device in a tunnel through the tissue of the patient.

6. The device of claim 1, wherein the central portion that forms the second eyelet has a fillet along at least a portion of the second eyelet facing the first foot of the device and along a portion facing the projection.

7. The device of claim 1, wherein at least one of the first eyelet and the second eyelet are tear-drop shaped.

8. The device of claim 1, wherein the spine is configured to form a second eyelet, and wherein the spine forms a slit that forms an opening to communicate with the second eyelet.

9. A system for use during a surgical procedure, the system comprising:
    a loop;
    one or more sutures; and
    a device configured to be positioned within a patient, wherein the device includes a spine, a first foot coupled to the spine and positioned at a first longitudinal end of the device, and a second foot connected to the spine and forming a second longitudinal end of the device, wherein a proximal surface of the spine has a convex arcuate curvature along substantially an entirety of a longitudinal axis of the device from the first longitudinal end to the second longitudinal end, wherein the spine includes a first eyelet configured to couple with the one or more sutures adjacent and proximal of a first proximally facing surface and a second proximally facing surface of the first foot and a second eyelet at a central portion of the spine, wherein the second eyelet is at least partially formed by a projection from a distal surface of the spine and is configured to couple with the loop, wherein each of the first foot and the second foot has a width of a larger dimension relative to a corresponding width of the spine along a longitudinal axis of the device, wherein the width of the first foot, the second foot and the width of the spine are measured in a direction transverse to a longitudinal axis of the device, wherein the width of the second foot exceeds the width of the first foot, and wherein the width of the first foot is configured to deter a passage of the device through a tunnel in soft tissue used for passage of the one or more sutures.

10. The system of claim 9, wherein the spine has a slit that forms an opening that communicates with the second eyelet from the proximal surface of the device, and wherein the loop comprises an adjustable loop that is passed through at least three openings of the second eyelet including the opening into the second eyelet.

11. The system of claim 9, further comprising a graft, wherein the graft is coupled to the device via the loop.

* * * * *